United States Patent
Mast

(10) Patent No.: US 10,905,474 B2
(45) Date of Patent: Feb. 2, 2021

(54) SURGICAL CORD TENSIONING DEVICES, SYSTEMS, AND METHODS

(71) Applicant: Zimmer Biomet Spine, Inc., Westminster, CO (US)

(72) Inventor: Randall G. Mast, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 123 days.

(21) Appl. No.: 16/115,441

(22) Filed: Aug. 28, 2018

(65) Prior Publication Data

US 2019/0059958 A1    Feb. 28, 2019

Related U.S. Application Data

(60) Provisional application No. 62/551,379, filed on Aug. 29, 2017.

(51) Int. Cl.
| A61B 17/70 | (2006.01) |
| A61B 17/88 | (2006.01) |
| A61B 90/00 | (2016.01) |

(52) U.S. Cl.
CPC ...... *A61B 17/7083* (2013.01); *A61B 17/7022* (2013.01); *A61B 17/7085* (2013.01);
(Continued)

(58) Field of Classification Search
CPC ............ A61B 17/7083; A61B 17/7022; A61B 17/8869; A61B 17/7091
See application file for complete search history.

(56) References Cited

U.S. PATENT DOCUMENTS

| 5,423,848 A | 6/1995 | Washizuka et al. |
| 6,251,111 B1 | 6/2001 | Barker et al. |

(Continued)

FOREIGN PATENT DOCUMENTS

| EP | 2047813 | 4/2009 |
| WO | 2019046339 | 3/2019 |
| WO | WO-2020077029 A1 | 4/2020 |

OTHER PUBLICATIONS

"International Application Serial No. PCT US2018 048403, International Search Report dated Nov. 15, 2018", 5 pgs.
(Continued)

*Primary Examiner* — Ellen C Hammond
(74) *Attorney, Agent, or Firm* — Schwegman Lundberg & Woessner, P.A.

(57) ABSTRACT

Implementations described herein may include a system for manipulating implants coupled by a cord. The system may include a tensioner and a counter tensioner. The tensioner may include a nose assembly and a cord lock assembly for applying tension to the cord. The nose assembly may include a piston having a lumen extending therethrough for receiving the cord and a spring positionable in contact with an indicator region of the piston. The counter may be releasably coupleable to a head of an implant at a proximal end thereof and may guide the cord to a port proximate the distal end thereof, the port for receiving the nose assembly. The counter tensioner may enable translation of the implant relative to another implant implanted in an adjacent or nearby vertebrae. The indicator region of the piston may be visible through a window in a tensioner main body and may indicate cord tension when the nose assembly of the tensioner is coupled to the port of the counter tensioner and engaged with the cord.

20 Claims, 11 Drawing Sheets

(52) U.S. Cl.
CPC ...... *A61B 17/7091* (2013.01); *A61B 17/8869* (2013.01); *A61B 2090/064* (2016.02)

(56) References Cited

U.S. PATENT DOCUMENTS

| | | | |
|---|---|---|---|
| 6,296,643 | B1 | 10/2001 | Hopf et al. |
| 7,073,415 | B2 | 7/2006 | Casutt et al. |
| 7,083,621 | B2 | 8/2006 | Shaolian et al. |
| 7,556,630 | B2 | 7/2009 | Molz, IV et al. |
| 7,909,826 | B2 | 3/2011 | Serhan et al. |
| 7,909,857 | B2 | 3/2011 | Ogilvie et al. |
| 8,118,841 | B2 | 2/2012 | Schwab |
| 8,123,749 | B2 | 2/2012 | Serhan et al. |
| 8,273,086 | B2 | 9/2012 | Serhan et al. |
| 8,308,771 | B2 | 11/2012 | Bennett et al. |
| 8,337,528 | B2 | 12/2012 | Ferree |
| 8,454,662 | B2 | 6/2013 | Bethell |
| 8,465,526 | B2 | 6/2013 | Friedrich et al. |
| 8,562,653 | B2 | 10/2013 | Alamin et al. |
| 8,591,560 | B2 | 11/2013 | Jackson |
| 8,632,572 | B2 | 1/2014 | Darst Rice et al. |
| 8,641,736 | B2 | 2/2014 | Marik et al. |
| 8,764,803 | B2 | 7/2014 | Suddaby |
| 8,888,818 | B2 | 11/2014 | Serhan et al. |
| 8,992,578 | B2 | 3/2015 | Slivka et al. |
| 9,011,498 | B2 | 4/2015 | Ogilvie et al. |
| 9,039,711 | B2 | 5/2015 | Mickiewicz et al. |
| 9,101,408 | B1 | 8/2015 | Dix |
| 9,211,142 | B2 | 12/2015 | Friedrich et al. |
| 9,277,940 | B2 | 3/2016 | Rice |
| 9,339,297 | B2 | 5/2016 | Friedrich et al. |
| 9,370,390 | B2 | 6/2016 | Mickiewicz et al. |
| 9,492,165 | B2 | 11/2016 | Serhan et al. |
| 9,526,525 | B2 | 12/2016 | Remington et al. |
| 9,833,275 | B2 | 12/2017 | Mickiewicz et al. |
| 2002/0032450 | A1 | 3/2002 | Trudeau et al. |
| 2005/0010220 | A1 | 1/2005 | Casutt et al. |
| 2007/0021737 | A1 | 1/2007 | Lee |
| 2007/0093846 | A1 | 4/2007 | Frigg et al. |
| 2007/0213714 | A1 | 9/2007 | Justis |
| 2008/0009863 | A1 | 1/2008 | Bond et al. |
| 2008/0077138 | A1 | 3/2008 | Cohen et al. |
| 2008/0132933 | A1 | 6/2008 | Gerber |
| 2008/0243052 | A1 | 10/2008 | Pond et al. |
| 2008/0287951 | A1 | 11/2008 | Stoneburner et al. |
| 2009/0054933 | A1 | 2/2009 | Mickiewicz et al. |
| 2009/0082776 | A1 | 3/2009 | Cresina |
| 2009/0088799 | A1 | 4/2009 | Yeh |
| 2009/0163962 | A1 | 6/2009 | Dauster et al. |
| 2009/0198281 | A1 | 8/2009 | Rice et al. |
| 2010/0042106 | A1 | 2/2010 | Bryant et al. |
| 2010/0168803 | A1 | 7/2010 | Hestad et al. |
| 2010/0318137 | A1 | 12/2010 | Stucki et al. |
| 2011/0060367 | A1 | 3/2011 | Stauber |
| 2011/0184473 | A1 | 7/2011 | Garcia-Bengochea et al. |
| 2012/0221054 | A1 | 8/2012 | Jackson |
| 2012/0259374 | A1 | 10/2012 | Marik |
| 2014/0243907 | A1 | 8/2014 | Cavallazzi et al. |
| 2014/0276051 | A1 | 9/2014 | Hoffman |
| 2015/0066042 | A1 | 3/2015 | Cummins et al. |
| 2015/0127003 | A1 | 5/2015 | Songer et al. |
| 2015/0209077 | A1 | 7/2015 | Marshall |
| 2015/0313644 | A1 | 11/2015 | Rice et al. |
| 2015/0342654 | A1 | 12/2015 | Gephart |
| 2016/0000468 | A1 | 1/2016 | Samdani et al. |
| 2016/0074147 | A1 | 3/2016 | Pereira et al. |
| 2016/0262811 | A1 | 9/2016 | Mickiewicz et al. |
| 2017/0027616 | A1 | 2/2017 | Serhan et al. |
| 2018/0029824 | A1 | 2/2018 | Gephart et al. |
| 2019/0059959 | A1 | 2/2019 | Serra et al. |
| 2019/0262039 | A1 | 8/2019 | Gordon et al. |
| 2019/0336182 | A1 | 11/2019 | Suh et al. |

OTHER PUBLICATIONS

"International Application Serial No. PCT US2018 048403, Written Opinion dated Nov. 15, 2018", 10 pgs.

"U.S. Appl. No. 16/156,158, Non Final Office Action dated Mar. 25, 2020", 15 pgs.

"International Application Serial No. PCT/US2018/048403, International Preliminary Report on Patentability dated Mar. 12, 2020", 12 pgs.

"International Application Serial No. PCT US2019 055511, International Search Report dated Jan. 21, 2020", 7 pages.

"International Application Serial No. PCT US2019 055511, Written Opinion dated Jan. 21, 2020", 10 pages.

"U.S. Appl. No. 16/156,158, Non Final Office Action dated Jul. 21, 2020", 15 pgs.

"U.S. Appl. No. 16/156,158, Response filed Jun. 24, 2020 to Non Final Office Action dated Mar. 25, 2020", 14 pgs.

"Australian Application Serial No. 2018323471, First Examination Report dated Jun. 15, 2020", 7 pgs.

"Australian Application Serial No. 2018323471, Response filed Aug. 27, 2020 to First Examination Report dated Jun. 15, 2020", 19 pgs.

500

502 — Insert counter tensioner and couple to bone implant

504 — Couple nose assembly of tensioner to port of counter tensioner

506 — Guiding a cord through the counter tensioner and securing in the tensioner 508 — Tensioning the cord by actuating a shaft clutch to translate the elongate shaft and cord 510 — Preventing proximal travel of the elongate shaft and cord with a shaft lock 512 — Translating the bone implant relative to an adjacent bone implant

*FIG. 6*

SURGICAL CORD TENSIONING DEVICES, SYSTEMS, AND METHODS

CLAIM OF PRIORITY

This application claims the benefit of U.S. Provisional Patent Application Ser. No. 62/551,379, filed on Aug. 29, 2017, the benefit of priority of which is claimed hereby, and which is incorporated by reference herein in its entirety.

BACKGROUND

Dynamic stabilization techniques, such as vertebral body tethering, are used in spinal treatment procedures for juveniles to permit enhanced mobility of the spine while also providing sufficient counter loading of a spinal curvature to effect treatment through bone growth modulation, particularly during times of rapid growth. Such dynamic stabilization systems may include pedicle screws installed in adjacent or nearby vertebrae of the spine and a flexible cord secured to the heads of the pedicle screws by set screws, with the cord under tension between pedicle screws.

SUMMARY

The present inventors have recognized, among other things, that improving ergonomics and ease of use of surgical cord tensioning devices, including enabling one handed use of a tensioner, may be desirable. The present inventors have also recognized that increasing cord travel per actuation cycle of the cord tensioner and providing a visual indication of cord load during tensioning may be desirable. The present specification discloses various methods, devices, systems, and embodiments that may include a cord tensioner that can be rigidly, removably coupleable to a port disposed on a distal end of a counter tensioner, wherein the proximal end of the counter tensioner can be rigidly, removably coupleable to a head of an implant. Accordingly, the present disclosure provides for a system for manipulating implants coupled by a cord. The system may comprise a tensioner and a counter tensioner. The tensioner can comprise a nose assembly and a cord lock assembly for applying tension to the cord. The nose assembly can comprise a piston having a lumen extending therethrough for receiving the cord and a spring positionable in contact with an indicator region of the piston. The counter tensioner can be releasably coupleable to a head of an implant at a proximal end thereof and can guide the cord to a port proximate the distal end thereof, the port for receiving the nose assembly. The counter tensioner may enable translation of the implant relative to another implant implanted in an adjacent or nearby vertebrae. Tension on the cord can be indicated through a window in a main body of the tensioner that provides visibility to an indicator region of the piston. The indicator region can indicate cord tension when the nose assembly of the tensioner is coupled to the port of the counter tensioner and engaged with the cord.

In another embodiment, the present disclosure provides for a method that can include the steps of inserting a counter tensioner into a patient and coupling the counter tensioner to an implant; coupling a nose assembly of a tensioner to a port of the counter tensioner; guiding a cord through the counter tensioner and securing the cord therein; tensioning the cord by actuating a shaft clutch to translate the elongate shaft and the cord; preventing proximal travel of the elongate shaft and cord via engagement of a shaft lock; and translating the implant relative to an implant in an adjacent or nearby bone.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6 is a flow chart illustrating steps in one exemplary method according to the present disclosure.

DETAILED DESCRIPTION

Exemplary embodiments will now be described more fully with reference to the accompanying drawings.

The present disclosure provides for a system comprising a cord tensioner that can be rigidly, removably coupleable to a port disposed on a distal end of a counter tensioner, wherein the proximal end of the counter tensioner can be rigidly, removably coupleable to a head of an implant. Such systems and methods of using the system can improve ergonomics and ease of use by, e.g., enabling one handed operation of a tensioner. Such systems can also increase cord travel per actuation cycle of the cord tensioner and provide a visual indication of cord load during cord tensioning.

Figure 1:
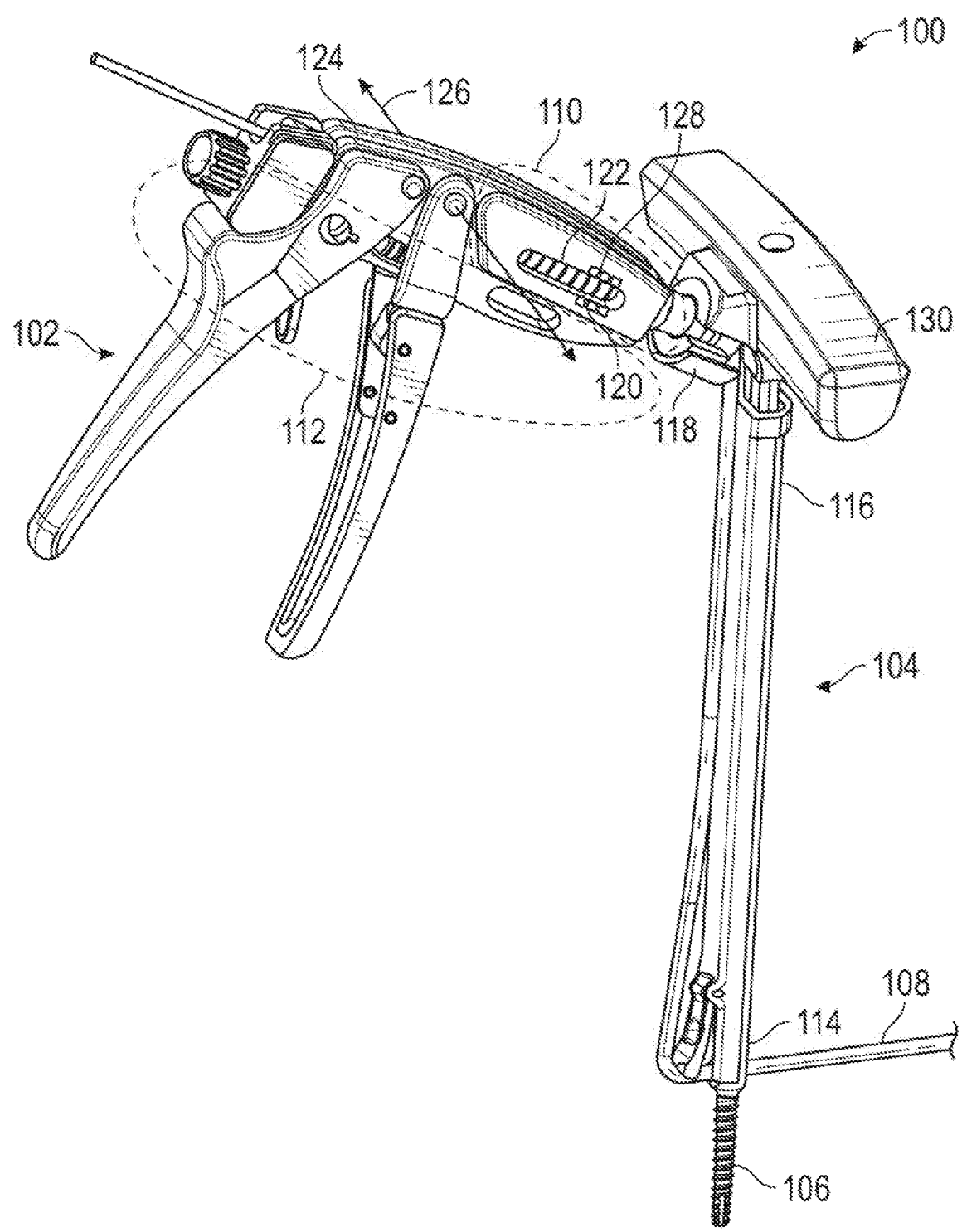
FIG. 1 is a perspective view of an embodiment of a system according to the present disclosure.
Figure 2:
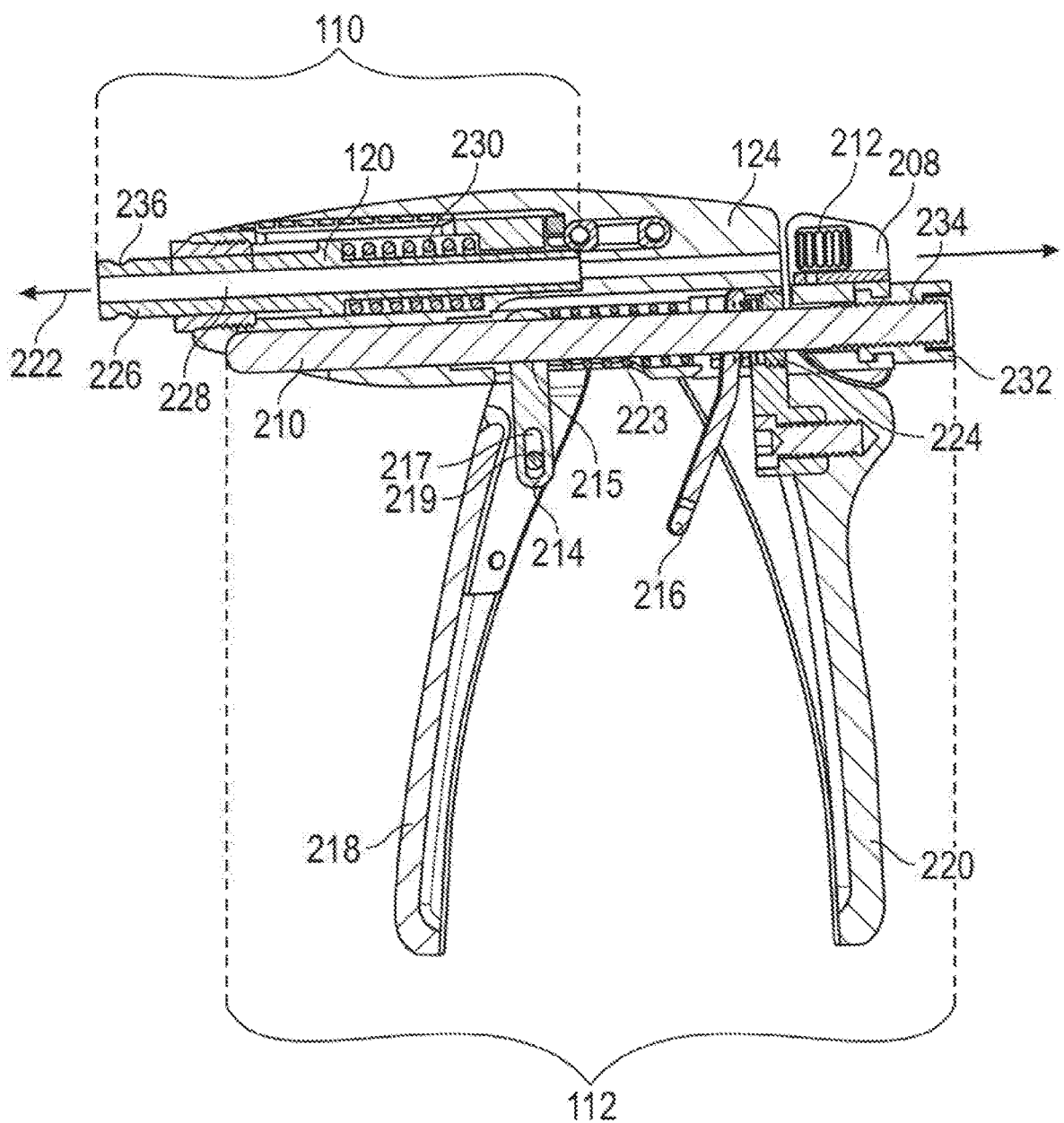
FIG. 2 is a cross-sectional view of one embodiment of a tensioner according to the present disclosure.

One exemplary embodiment of a system 100 according to the present disclosure is illustrated in FIGS. 1-3. The system 100 can comprise a tensioner 102 and a counter tensioner 104, which are used in combination for manipulating implants 106 coupleable by a cord 108. The tensioner 102 is designed to enable one-handed operation to apply tension to a cord 108. The tensioner 102 can comprise a nose assembly 110 for receiving the cord 108 and a cord lock assembly 112 for securing and applying tension to the cord 108. The counter tensioner 104 can be releasably coupleable to a head of an implant 106 at a distal end 114 thereof and can have a port 118 disposed in a proximal end 116 thereof. The port 118 can be releasably coupleable the nose assembly 110 of the tensioner 102. The counter tensioner 104 can further be rigidly coupleable to both the head of the implant 106 and the nose assembly 110, allowing a surgeon to tension the cord 108 via the tensioner 102 and translate the implant 106 and underlying vertebrae relative to another implant implanted in an adjacent or nearby vertebrae via a handle 130 in the same surgical step and as explained in greater detail below.

The implant 106 can be, for example and without limitation, a threaded fastener, a bone screw, a pedicle screw, a staple, a bone clamp, a universal bone clamp, cam blocks, bone plates, and the like. Furthermore, it is contemplated that the tensioner can be used to tension a cord between bones, clamps, or any implant secured to a bone in any manner. The implant 106 can comprise a shaft that purchases underlying bone and a head including features for securely engaging an elongate member that, prior to being secured, can be tensioned to apply forces to manipulate the position of adjacent or nearby vertebrae as a juvenile patient experiences growth. The cord can be, for example and without limitation, any elongate member including a cord, a tether, strap, a cable, a wire, a suture, a thread, or similar flexible ligature. In additional or alternative embodiments, the elongate member can have some beneficial temporal elastic properties that could, for example and without limitation, avoid overcorrection or under correction over the life of an implanted system, and the like. The term "cord" is used throughout the present disclosure, but should be understood to include any elongate member.

One exemplary embodiment of a tensioner 102 according to the present disclosure is illustrated in FIGS. 1-2. The tensioner 102 can comprise a nose assembly 110 and a cord lock assembly 112 for applying tension to the cord 108. The nose assembly 110 and the cord lock assembly 112 can be at least partially disposed in the main body 124 of the tensioner 102

The cord lock assembly 112 can comprise a cord lock housing 208 disposed at a distal end of an elongate shaft 210 and can engage a cord 108 therein. The cord lock housing 208 can comprise, for example and without limitation, a cam cleat 212 or the like for engaging and disengaging the cord 108. The elongate shaft 210 can be operably coupled to a shaft clutch 214 to drive the elongate shaft 210 distally and a shaft lock 216 that can resist return of the elongate shaft 210 in the proximal direction at the end point of an actuation cycle of the tensioner 102. The shaft clutch 214 can extend from a first end to a second end. The first end can have an opening 215 disposed therein for receiving the elongate shaft 210 and the second end has a slot 217 disposed therein that is transverse to a longitudinal axis of the elongate shaft 210. The slot 217 receives a pin 219 extending from a front handle 218. Actuation of the front handle 218 shifts the opening 215 disposed in the first end of the shaft clutch 214 off angle to engage and distally translate the elongate shaft 210 as the front handle 218 is actuated towards a stationary rear handle 220. The front handle 218 can be rotatable about a pivot axis 126 (shown in FIG. 1) that is transverse to a longitudinal axis 222 extending from a proximal end to a distal end of the main body. A shaft spring 223 positioned distal to the shaft clutch 214 and about the elongate shaft 210 can urge the shaft clutch 214 and front handle 218 back to the starting point of the actuation cycle of the tensioner 102. The shaft lock 216 can be biased via a distally-located lock spring 224 to allow distal translation but not proximal translation of the elongate shaft 210. The shaft lock 216 can be released by, articulating the shaft lock 216 distally if the tension on the cord 108 needs to be released, such as once the cord 108 is secured within the implant 106. Additionally or alternatively, a cord nut 232 disposed proximate a distal end of the cord lock housing 208 can be rotated to adjust the cord tension via engagement with threading 234 disposed on the distal end of the elongate shaft 210. In one example, the elongate shaft 210 can be distally translated from about 30 mm to about 35 mm during each actuation cycle or stroke of the shaft clutch 214. The tensioner 102 can be actuated via a single hand of a surgeon, freeing the other hand for performing other surgical tasks during and adjacent to cord tensioning.

The nose assembly 110 can comprise a piston 226 having a lumen 228 extending therethrough for receiving the cord and a load spring 230 positionable in contact with an indicator region 120 disposed on the piston 226. The indicator region 120 of the piston 226 can have a cross-sectional diameter than can be greater than or equal to any other portion of the piston 226. A nose cap can retain the piston 226 and load spring 230 in the main body 124 of the tensioner 102. The load spring 230 can be calibrated so that the position of the indicator region 120 of the piston 226 correlates to the load applied to the cord as the cord 108 is tensioned and there is a counter pressure applied by the counter tensioner 104 to the nose assembly 110. The indicator region 120 can be visible through a window 122 disposed on the main body 124 of the tensioner 102 having indicia 128 printed adjacent thereto indicative of cord load at various indicator region positions relative to the tensioner main body 124, as best illustrated in FIG. 1. The piston 226 can have a detent 236 disposed in a circumferential outer surface of the piston 226 proximate a proximal end thereof for coupling to the counter tensioner 104.

Figure 3A:
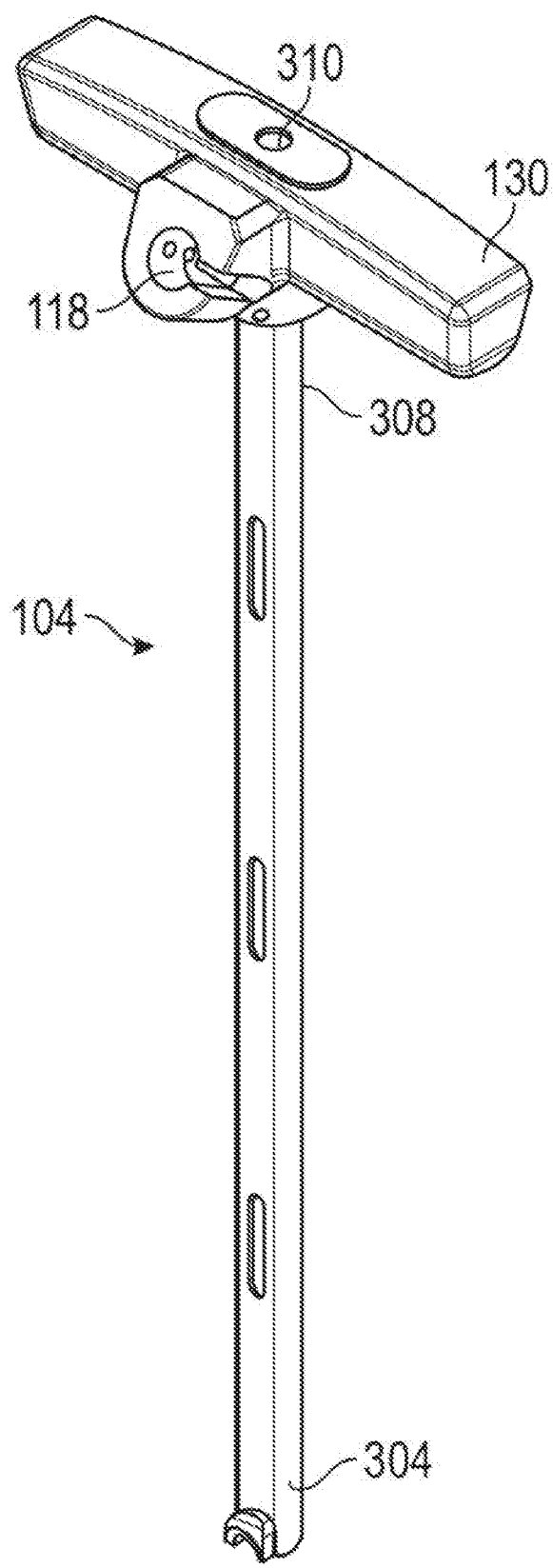
FIG. 3A is a perspective view of an embodiment of a counter tensioner according to the present disclosure and FIG. 3B is an exploded view of the counter tensioner of FIG. 3A.
Figure 3B:
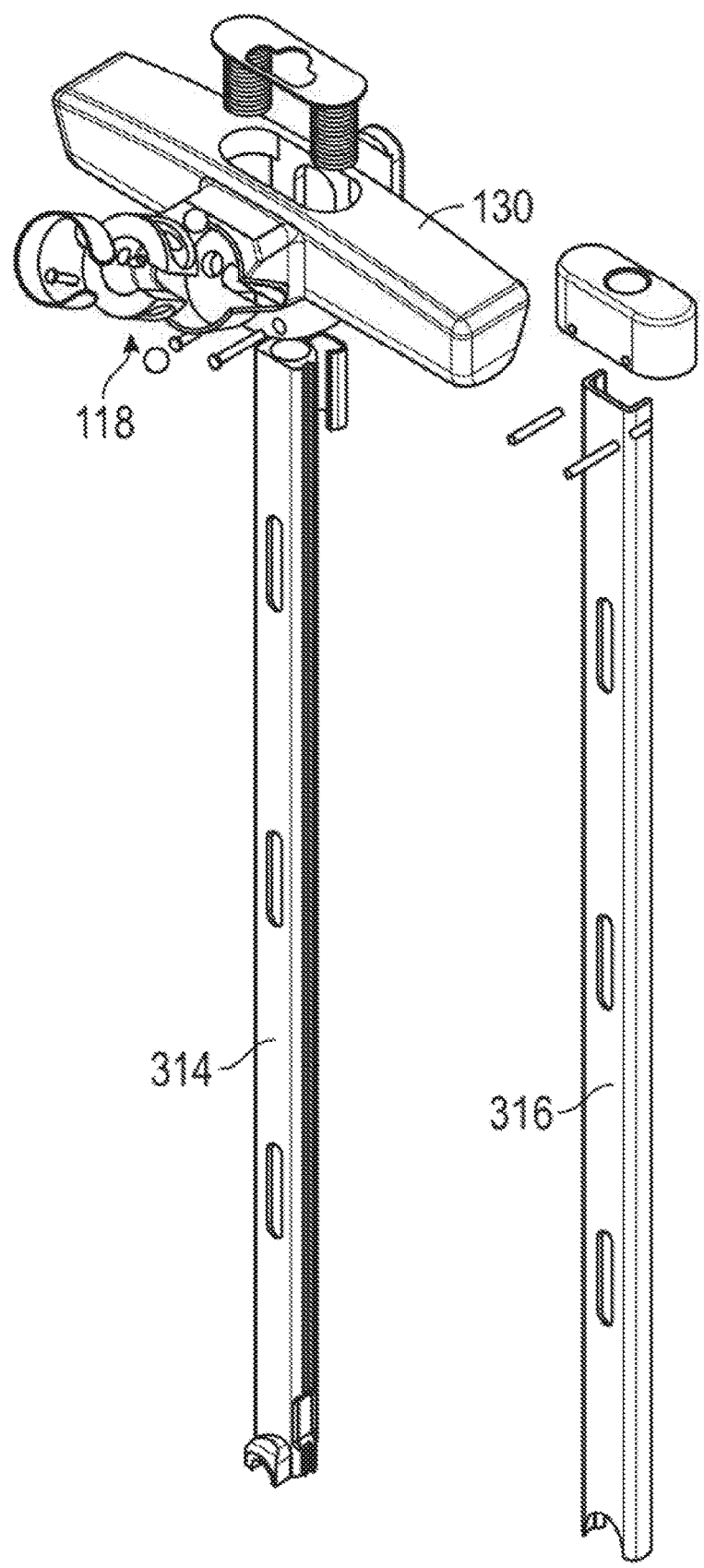
Figure 4A:
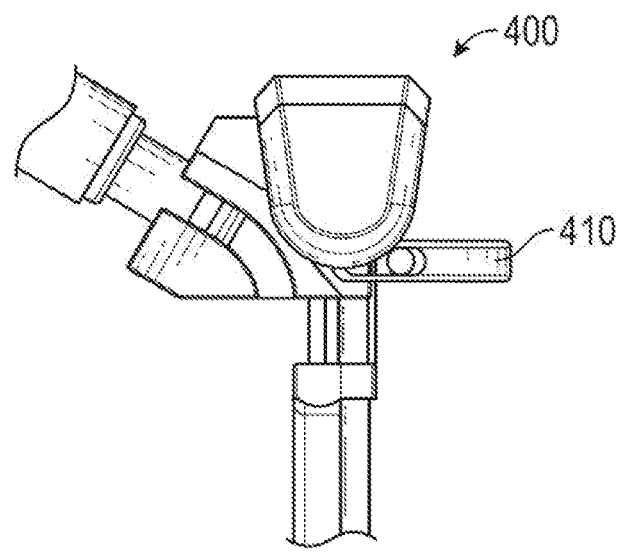
FIG. 4A is a partial perspective view of an embodiment of a proximal end of the system in use in a first position and FIG. 4B is a partial perspective view of the distal end of the embodiment of FIG. 4A in use.
Figure 4B:
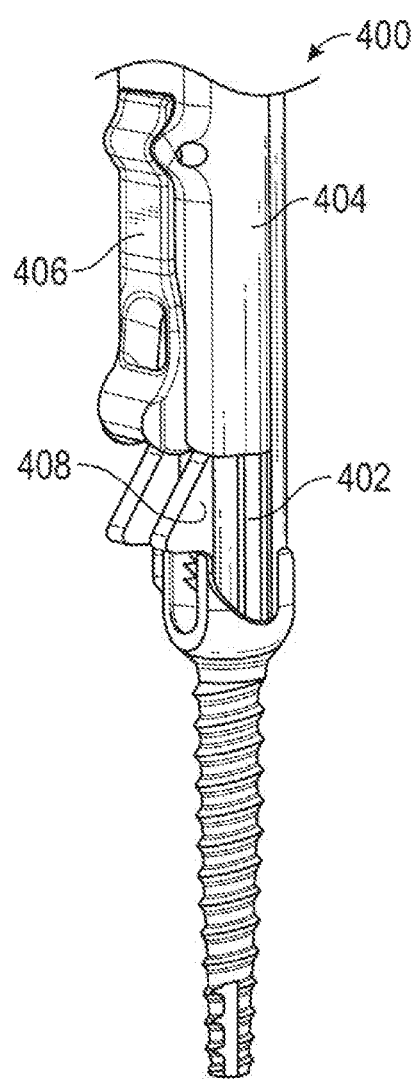
Figure 5A:
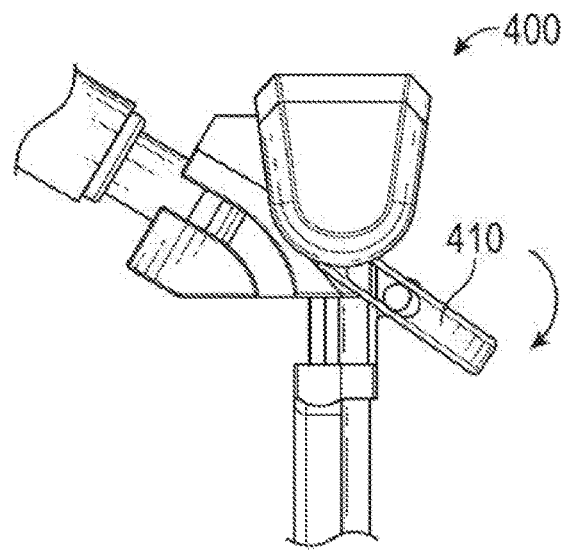
FIG. 5A is a partial perspective view of an embodiment of a proximal end of the system in use in a second position and FIG. 5B is a partial perspective view of the distal end of the embodiment of FIG. 5A in use.
Figure 5B:
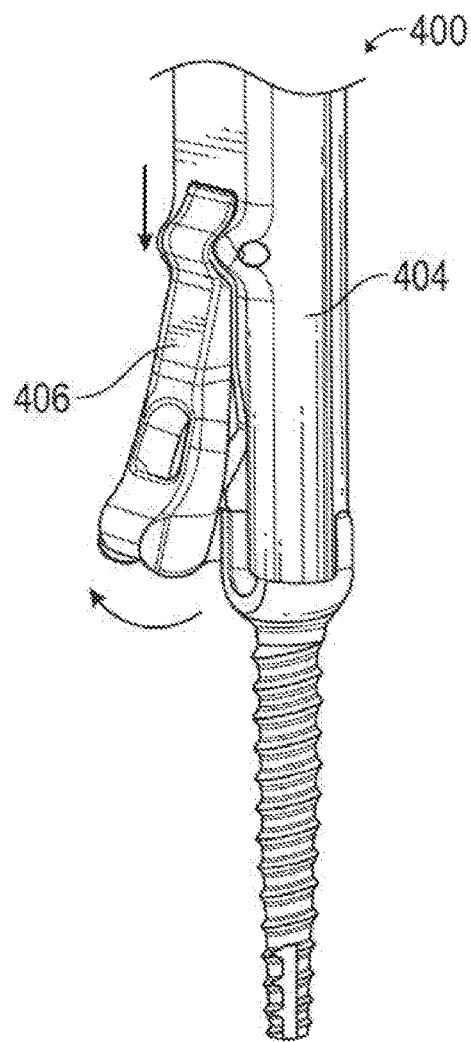

One exemplary embodiment of a counter tensioner 104 according to the present disclosure is illustrated in FIGS. 1, 3A, and 3B. The counter tensioner 104 can be releasably coupleable to the head of an implant 106 at a distal end 304 thereof. The counter tensioner 104 can guide the cord 108 to a port 118 proximate the proximal end 308 thereof. The port 118 can allow the cord to be fed through the nose assembly 110 to be secured in the cord lock housing 208 of the cord lock assembly 112. The port 118 can rigidly, releasably receive the nose assembly 110 of the tensioner 102 via a capture ball disposed in the port 118 for engaging the detent 236 of the piston 226. The counter tensioner 104 can further comprise a lumen 310 disposed therein extending from the distal end 304 to the proximal end 308 thereof. The port 118 can be disposed at an angle that is not parallel to a longitudinal axis of the lumen 310. A set screw (not shown) can be deliverable through the lumen 310 and engageable with the head of the implant to secure the cord therein with a driver (not shown). The counter tensioner 104 can comprise a handle 130 that can facilitate translation of the implant 106 relative to another implant implanted in an adjacent or nearby vertebrae. Accordingly, vertebral translation, cord tensioning, and cord fixation can be performed in the same surgical step.

The counter tensioner 104 can further comprise an inner sleeve 314 and an outer sleeve 316. The inner sleeve 314 can comprise a plurality of outwardly biased arms at a distal end thereof that are engageable with cooperating features disposed on the head of the implant. Advancing the outer sleeve 316 distally over the inner sleeve 314 and at least partially over the head of the implant can urge the outwardly biased arms into secure engagement with cooperating features on the head of the implant.

Another exemplary embodiment of a counter tensioner 400 according to the present disclosure is illustrated in FIGS. 4A-5B. Here, the counter tensioner 400 can comprise an inner sleeve 402 and an outer sleeve 404. A distal end of the outer sleeve 404 comprises a fulcrum 406 that can move from a first position where the fulcrum 406 is parallel to a longitudinal axis of the counter tensioner 400 to a second position where the fulcrum 406 pivots outwardly from the longitudinal axis of the counter tensioner 400. The inner sleeve 402 can comprise at least one projection 408 that can urge the fulcrum 406 outward as the outer sleeve 404 passes distally over the inner sleeve 402 and at least partially over the head of the implant. The fulcrum 406 serves to change the cord angle, easing local tension on the cord as it is routed up to the tensioner 102 engaged in the port 118. Optionally, a pivoting latch 410 can be provided at a proximal end of the inner sleeve 402. The pivoting latch 410 can be operatively coupled to the counter tensioner 400 so that the pivoting latch 410 moves downward as the fulcrum moves toward a parallel orientation relative to the longitudinal axis of the counter tensioner 400 and upward as the fulcrum pivots outwardly from the longitudinal axis of the counter tensioner. As a skilled artisan will appreciate in light of the present disclosure, the fulcrum can reduce stress applied to the cord during the tensioning process.

FIG. 6 is a flowchart illustrating a method 500 according to an exemplary embodiment. The method 500 can include operations such as coupling a counter tensioner to an implant at 502; coupling a tensioner to the counter tensioner at 504; routing a cord through the counter tensioner and securing the cord in the tensioner at 506; and tensioning the cord at 508. The method 500 can begin at 502 with a counter tensioner, such as counter tensioner 104, being inserted through an incision and coupled to a head of an implant. In an example, the counter tensioner 104 includes an inner sleeve (e.g., inner sleeve 314) including biased arms located at a distal end thereof and an outer sleeve (e.g., outer sleeve 316). In this example, the biased arms can be engaged with cooperating features on the head of the implant, and the outer sleeve can subsequently be slid distally to lock the biased arms onto the head of the implant. In another example, the counter tensioner can include a threaded feature, a quick connect feature, or the like at a distal end thereof to couple the counter tensioner 104 to complementary features disposed on the head of the implant. In yet another additional or alternative example, the counter tensioner 104 can engage the head of the implant such that the longitudinal axis of the implant and the longitudinal axis of the counter tensioner are not parallel and the cord can couple the counter tensioner to the implant.

At 504, the method 500 can continue with the tensioner 102 being coupled to the counter tensioner 104. In an example, the tensioner 102 includes a nose assembly 110 including a piston 226 formed from a cylinder with a detent 236 disposed in a circumferential outer surface and proximate a proximal end thereof. The detent 236 in the piston 226 can engage a capture ball biased into the port 118.

At 506, the method 500 can continue with guiding a cord from the proximal end of the counter tensioner 104, through the port 118 and a lumen 228 disposed in a piston 226 of the nose assembly 110 of the tensioner 102, and securing the cord within a cord lock housing 208 of a cord lock assembly 112 disposed at the end of an elongate shaft 210, the cord being secured in an implant 106 in an adjacent or nearby vertebrae.

At 508, the method 500 can continue with tensioning the cord 108 by actuating a front handle 218 of the tensioner 102 to cause a shaft clutch 214 to engage and distally translate the elongate shaft 210 and the cord 108.

At 510, the method 500 can continue by preventing proximal travel of the elongate shaft 210 at the end of the stroke of the shaft clutch 214 by causing the shaft lock 216 to engage and prevent return of the elongate shaft 210.

At 512, the method 500 can include translating the implant and underlying vertebrae relative to an implant of an adjacent or nearby vertebrae. Here, a surgeon can grasp handle 130 to translate the implant coupled to the counter tensioner 104. The steps of tensioning the cord and translating the vertebrae can be performed simultaneously.

The method can further comprise indicating a load on the cord by the position of an indicator region of a piston of the nose assembly relative to indicia printed adjacent a window in a main body of the tensioner. As the cord is tensioned and counter pressure is applied to the piston of the nose assembly, the piston depressed the load spring and an indicator region of the piston moves in the window disposed in the main body relative to the printed indicia printed adjacent to the window to indicate the load applied to the cord.

Another exemplary embodiment of a cord tensioning system, system 700, is illustrated in FIGS. 7A-7G. The system 700 can comprise a tensioner 702 and a counter tensioner 704, which are used in combination for manipulating implants 106 coupleable by a cord 108 (not illustrated in conjunction with this example). The tensioner 702 is designed to enable one-handed operation to apply tension to a cord 108 (similar to that shown in FIG. 1). The tensioner 702 includes similar structural features to tensioner 102 discussed in reference to FIGS. 1-3, and will not be further described in reference to this example. The counter tensioner 704 can be releasably coupleable to a head of an implant 106 at a distal end 714 thereof and can have a port 718 disposed in a proximal end 716 thereof. The port 718 can releasably receive the nose assembly of the tensioner 702 (tensioner 102 is interchangeable with tensioner 702). The counter tensioner 704 can further be rigidly coupleable to both the head of the implant 106 and the nose assembly, allowing a surgeon to tension the cord 108 via the tensioner 702 and translate the implant 106 and underlying vertebrae relative to another implant implanted in an adjacent or nearby vertebrae via a handle 730 in the same surgical step and as explained in greater detail below. The remaining discussion of counter tensioner 704 focuses on the aspects that differ from examples discussed above.

In this example, the counter tensioner 704 includes a handle 730 with additional features, such as a lock position 732, an unlock position 734, and a lock handle 736. The lock handle 736 is rotatable between the lock position 732 and the unlock position 734. In the unlock position 734, the counter tensioner 704 can be inserted over an implant, such as implant 106 (e.g., a pedicle screw). Once inserted over the pedicle screw, the lock handle 736 can be rotated into the lock position 732 and elements discussed below will lock the counter tensioner 704 to the pedicle screw. Internal workings of the lock mechanism are discussed in reference to FIGS. 7F and 7G below.

Figure 7A:
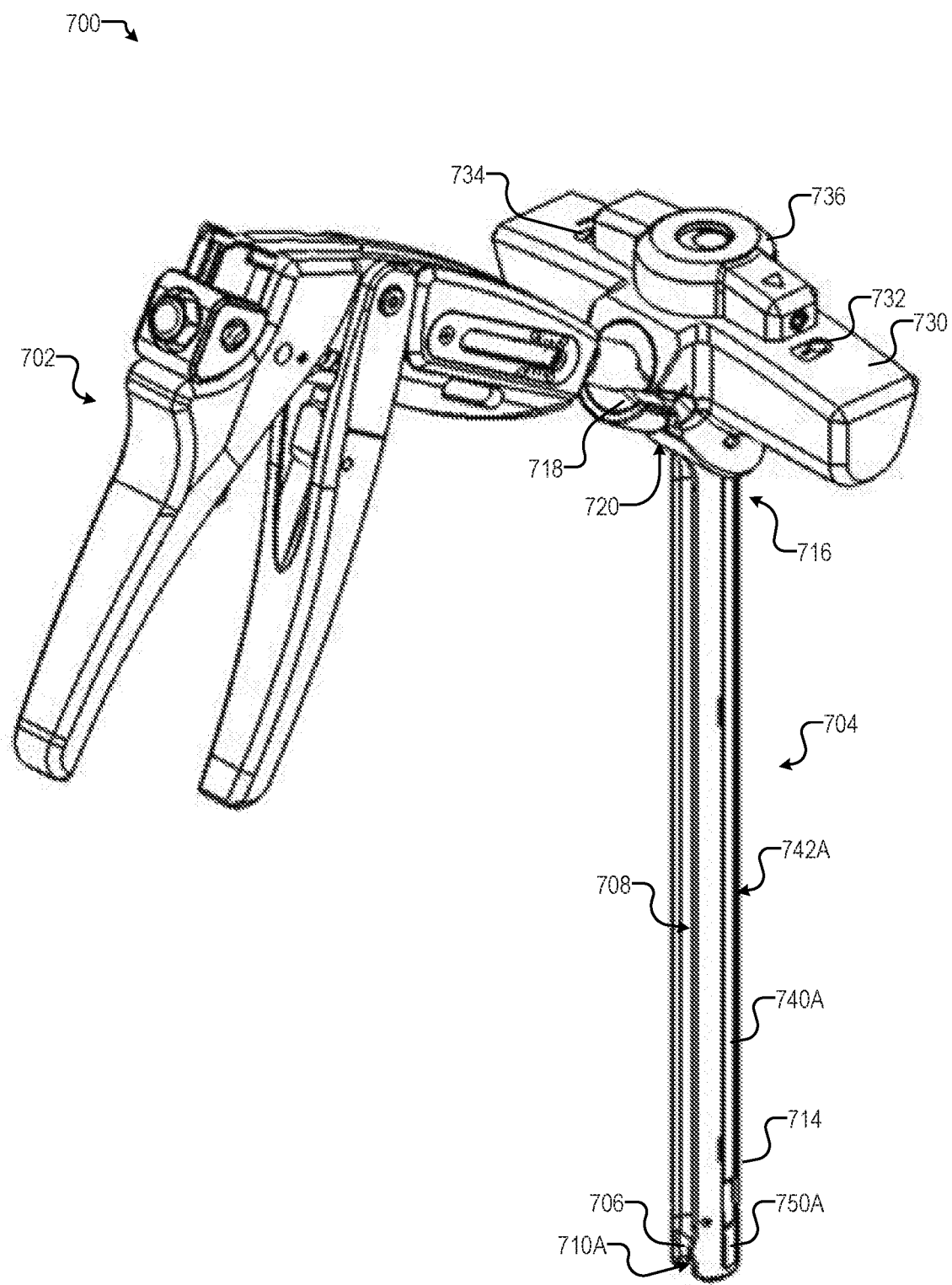
FIGS. 7A-7G illustrate a cord tensioning system, according to various embodiments of the present disclosure.
Figure 7B:
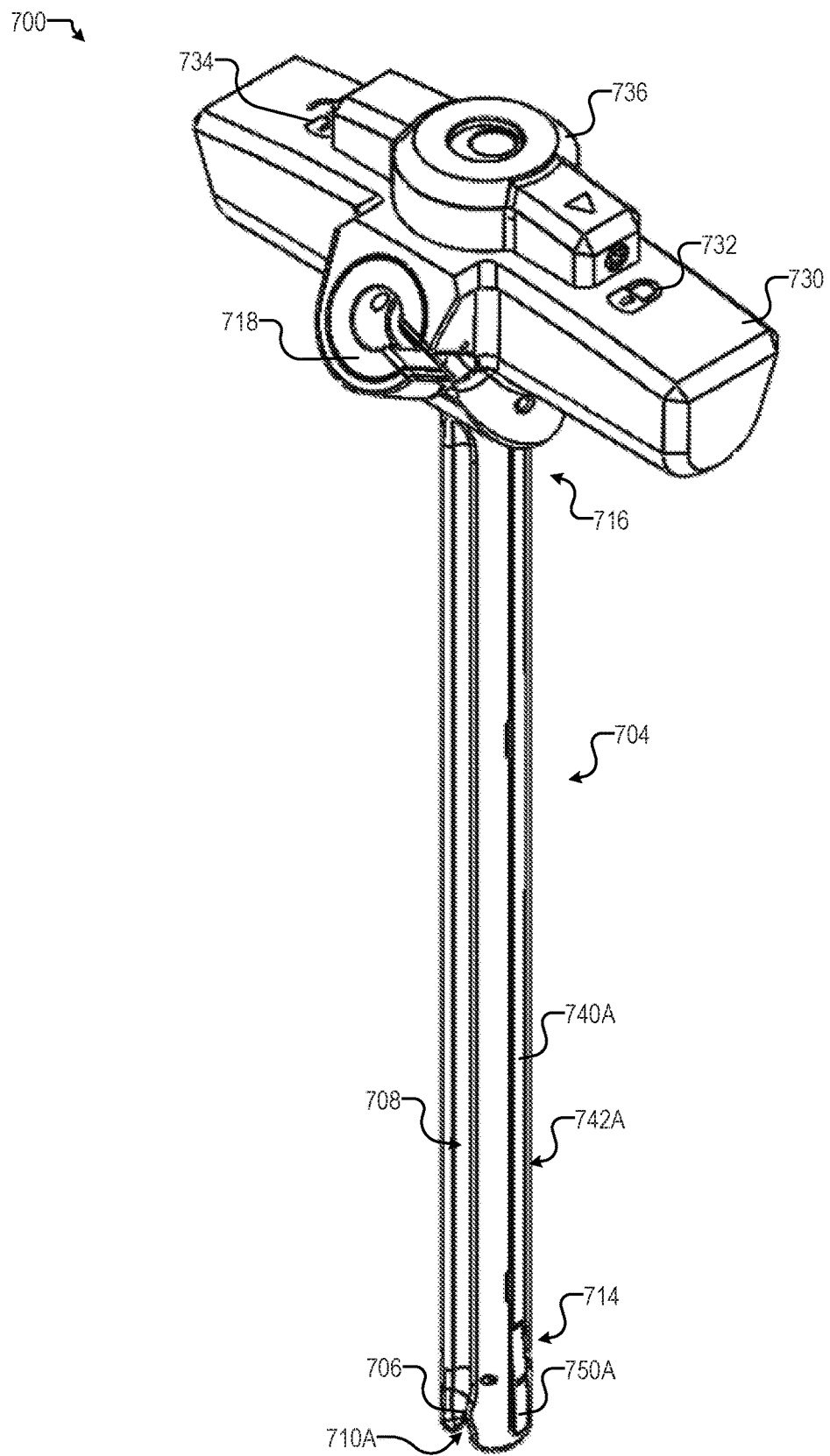

Along the length of the counter tensioner 704 extend a pair of locking extensions 740A, 740B within a pair of locking extension channels 742A, 742B. FIGS. 7A-7B only illustrate locking extension 740A and locking extension channel 742A. In this example, the locking extensions 740A, 740B are square elongate members connected at a proximal end to a locking mechanism operated by the lock handle 736. In other examples, the locking extensions 740A, 740B can be cylindrical rods or other cross-sectional profiles. The locking extension channels in this example are open square (or rectangular) channels, designed to fit the locking extensions 740A, 740B. Moving to the distal end 714 of the counter tensioner 704, the locking extension 740A engages one of the pivot locks 750A (pivot lock 750B is disposed on the opposite side, and shown in FIGS. 7D and 7E). In other examples, the locking extension channels can be a different cross sectional shape and/or be internal to the counter tensioner 704. FIGS. 7A and 7B also illustrate a cord fulcrum 706, a cord channel 708, and a cord guide 710A (cord guide 710B is an opening on the opposing side of the distal end 714 not illustrated in this example). The cord guide 710A allows the cord to exit the counter tensioner 704 and pedicle screw. The cord guides 710A, 710B are designed to complement the U-shaped pedicle screw head adapted to receive the cord. The cord fulcrum 706 includes an enlarged radius area to smooth directional change in the cord from a first direction essentially transverse to a longitudinal axis of the counter tensioner 704 to a second direction essentially parallel the longitudinal axis (see FIG. 1, the cord fulcrum 706 operates in a manner similar to fulcrum 106). In contrast to fulcrum 106, the cord fulcrum 706 is an integral part of the distal end 714, and does not include any moving parts (e.g., does not pivot). From the cord fulcrum 706, the cord extents proximally along the cord channel 708 until entering the cord conduit 720 at the base of the tensioner port 718, which is more clearly illustrated in FIG. 7G. The cord channel 708, in this example, is a semi-circular recess in the elongate portion of the counter tensioner 704.

Figures 7C, 7D:
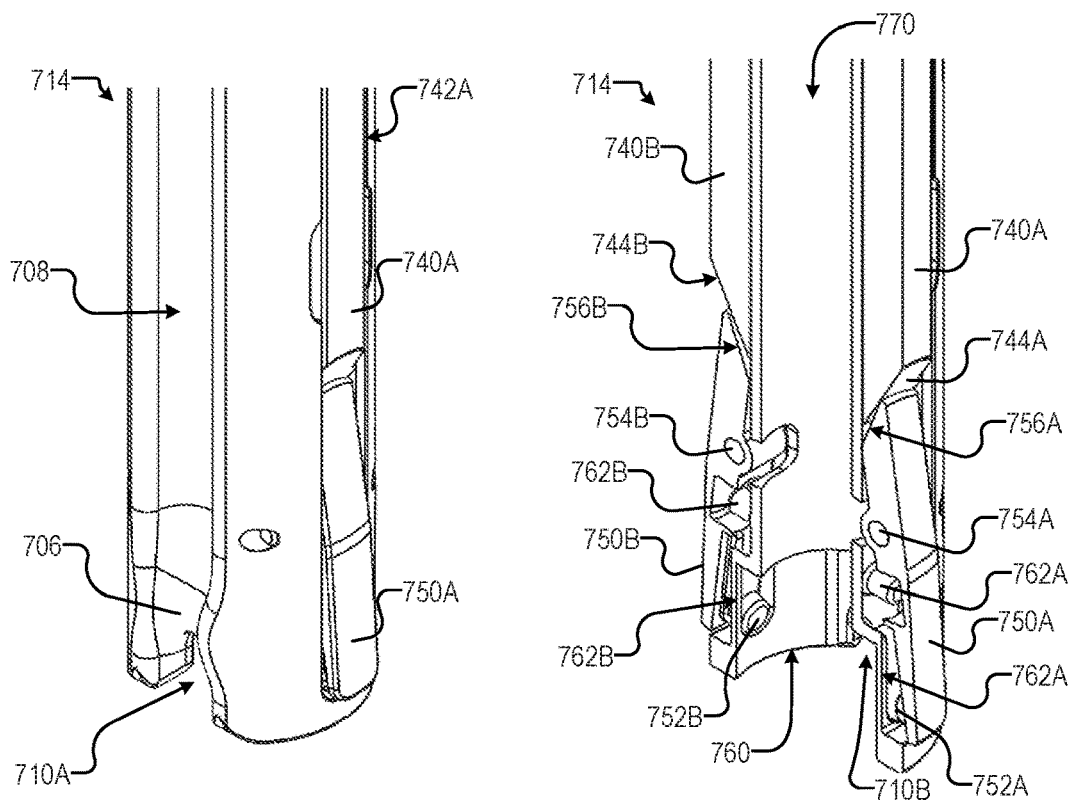

FIG. 7C is a close-up perspective view of the distal end 714 of the counter tensioner 704. A number of the structures discussed above are shown in additional detail, including the cord fulcrum 706, the cord channel 708, the cord guide 710A, a distal end of the locking extension 740A, the locking extension channel 742A, and the pivot lock 750A. FIG. 7C illustrates the counter tensioner 704 in an unlocked position. The cord fulcrum 706 in particular is shown in greater detail, in this figure it is easier to make out the radius created by the cord fulcrum 706. The enlarged radius provides a smoother transition for the cord coming out of the cord guide 710A and proceeding up along the cord channel 708.

Figure 7E:
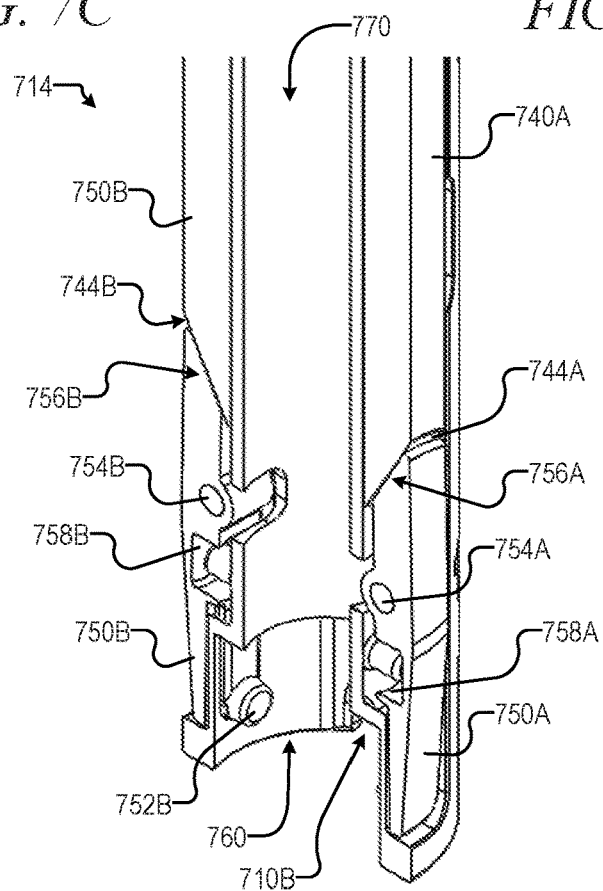

FIGS. 7D and 7E provide cross sectional views of the distal end 714 of the counter tensioner 704 in an unlocked and locked state, respectively. The cross sections provide a detailed view of both sides of the counter tensioner 704. For example, both locking extensions 740A, 740B are shown extending down opposite sides of the counter tensioner 704 and terminating in extension wedges 744A, 744B. The extension wedges 744A, 744B tapper the locking extensions 740A, 704B down to a thin edge along the distal most portion. In this example, the extension wedges 744A, 744B tapper at approximately 60 degrees, but other tappers can be used. The extension wedges 744A, 744B engage with lock wedges 756A, 756B, respectively. The lock wedges 756A, 756B in this example tapper at a corresponding amount to produce an essentially opposing structure to the extension wedges 74A 744B. In some examples, the ramp (tapper) angle on the lock wedges 756A, 756B is slightly greater or slightly less than the extension wedges 756A, 756B to reduce friction between the surfaces. The locking mechanism within the handle 730 operates to linearly translate the locking extensions 740A, 740B from the unlocked position shown in FIG. 7D to a locked position shown in FIG. 7E. Upon translation, the extension wedges 744A, 744B engage the lock wedges 756A, 756B and cause the pivot locks 750A, 750B to rotate about pivots 754A, 754B to shift locking pins 752A, 752B into recesses within a head of the pedicle screw. The pivot locks 750A, 750B are biased into an unlocked position by springs (not shown for clarity) disposed within spring recesses 758A, 758B with the springs held in place by spring pins 764A, 764B. The locking pins 752A, 752B operate to secure the counter tensioner 704 on the pedicle screw head when pivoted into the locked position (FIG. 7E). In this example, the locking pins 752A, 752B are cylindrical posts extending radially inward. In other examples, the locking pins 752A, 752B can be different cross-sectional shapes, such as square or rectangular. The pedicle screw is also surrounded by the pedicle screw receptacle 760 that includes pin openings 762A, 762B to receive the locking pins 752A, 752B, respectively. Pedicle screw receptacle 760 receives the longitudinal bore 770, which extends the length of the counter tensioner 704. The longitudinal bore 770 can allow for insertion of a closure top (e.g., set screw) into the pedicle screw to secure the cord. Finally, FIGS. 7D and 7E illustrate cord guide 710B with opposing cord guide 710A shown in FIG. 7C.

Figure 7F:
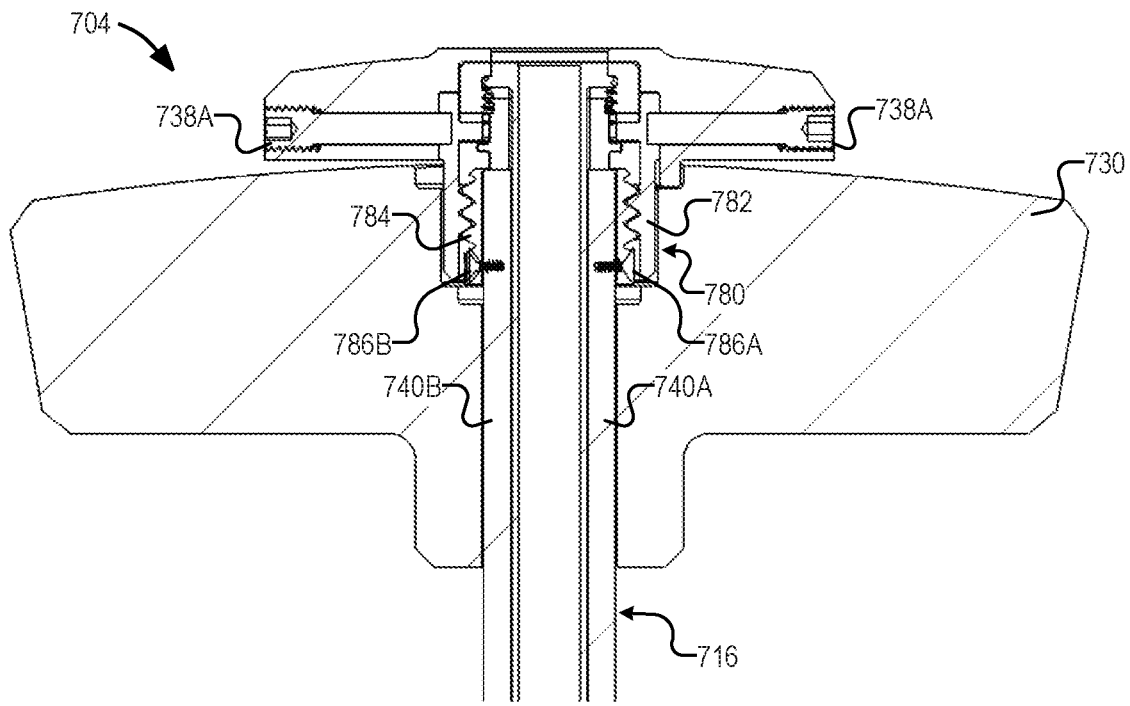
Figure 7G:
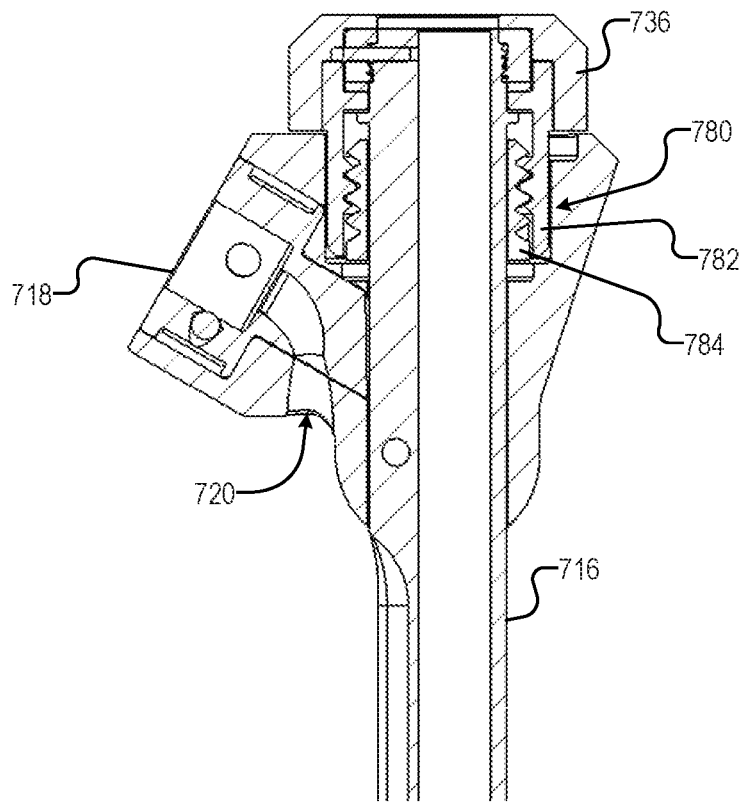

FIGS. 7F and 7G provide cross sectional views of the proximal end 716 of the counter tensioner 704. The cross sectional views include details of the proximal lock mechanism 780 and interaction with the lock handle 736. The proximal lock mechanism 780 operates to linearly translate the locking extensions 740A, 740B, which in turn shift the pivot locks 750A, 750B from an unlocked to locked position as discussed above. The proximal lock mechanism 780 includes a lock cylinder 782 coupled to the lock handle 736 through two lock cylinder set screws 738A, 738B. The lock handle 736 rotates the lock cylinder 782, which in turn causes translation of the locking extension 740A, 740B. The translation is accomplished, in this example, through interaction between a threaded cylinder 784 and a threaded internal portion of the lock cylinder 782. The threaded cylinder 784 is coupled to the locking extensions 740A, 740B through extension coupling pins 786A, 786B. When the lock handle 736 is rotated, the lock cylinder 782 rotates with an internal threaded surface engaging the external threads on the threaded cylinder 784, which is coupled to the locking extensions. As the lock handle 736 and lock cylinder are coupled to the elongate portion of the counter tensioner 704, the threaded interaction causes the threaded cylinder 784 and locking extensions 740A, 740B to translate in a proximal-distal direction. Other mechanisms for translating the locking extensions 740A, 740B can be utilized without deviating from this basic design, such as a cam follower arrangement between the lock cylinder 782 and locking extensions 740A, 740B.

FIG. 7G also provides illustration of the cord conduit 720 leading to the tensioner port 718. As discussed above, the cord can be routed out of the cord guide 710A, around the cord fulcrum 706, proximally along the cord channel 708, through the cord conduit 720, and into the tensioner 702 through the tensioner port 718.

Each of the above non-limiting examples can stand on its own, or can be combined in various permutations or combinations with one or more of the other examples.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure.

Example 1 is a system for manipulating implants coupled by a cord and/or tensioning a cord extending between two or more implants. The system can include a tensioner and a counter tensioner. The tensioner can include a nose assembly and a cord lock assembly for applying tension to the cord, the nose assembly can comprise a piston having a lumen extending therethrough for receiving the cord and a spring positionable in contact with an indicator region of the piston. The counter tensioner operates to guide the cord from the tensioner to an implant. The counter tensioner can include an elongate body with a proximal end and a distal end, where the proximal end includes a port to receive the nose assembly. The distal end of the counter tensioner is releasably coupleable to a head of the implant enabling translation of the implant relative to another implant implanted in an adjacent or nearby vertebrae. The tensioner indicator region can be visible through a window in a tensioner main body and indicates cord tension when the nose assembly of the tensioner is coupled to the port of the counter tensioner and engaged with the cord.

In example 2, the subject matter of example 1 includes the counter tensioner having a lumen disposed within the elongate body and extending from the proximal end to the distal end thereof, and a set screw engageable with the head of the implant to fix the cord is deliverable through the lumen.

In example 3, the subject matter of any one of examples 1 or 2 includes the port within the counter tensioner being disposed at an angle that is not parallel to a longitudinal axis of the lumen.

In example 4, the subject matter of any one of examples 1 to 3 includes the nose assembly of the tensioner having a detent releasably coupleable in the port via a capture ball.

In example 5, the subject matter of any one of examples 1 to 4 includes the counter tensioner including an inner sleeve and an outer sleeve, the inner sleeve comprising a plurality of outwardly biased arms at a distal end thereof that are engageable with cooperating features disposed on the head of the implant when the outer sleeve is translated distally over the inner sleeve and at least partially over the head of the implant to urge the plurality of outwardly biased arms into secure engagement with the cooperating features of the head of the implant.

In example 6, the subject matter of any one of examples 1 to 5 includes the cord lock assembly of the tensioner including a cord lock housing for engaging the cord disposed at a distal end of an elongate shaft.

In example 7, the subject matter of example 6 includes the cord lock housing having a cam cleat for engaging the cord.

In example 8, the subject matter of any one of examples 6 or 7 includes the elongate shaft being operably coupled to a shaft clutch to drive the elongate shaft distally and a shaft lock to resist return of the elongate shaft in the proximal direction.

In example 9, the subject matter of example 8 includes the shaft clutch being shifted off angle to engage and distally translate the elongate shaft by actuation of a front handle.

In example 10, the subject matter of example 9 includes the front handle being rotatable about pivot axis that is transverse to a longitudinal axis extending from a proximal end to a distal end of the tensioner main body.

In example 11, the subject matter of any one of examples 9 or 10 includes the shaft lock being biased via a distally-located spring to allow distal translation but not proximal translation of the elongate shaft.

In example 12, the subject matter of example 8 includes the elongate shaft being distally translated from about 30 mm to about 35 mm during each complete stroke of the front handle.

In example 13, the subject matter of any one of examples 1 to 12 includes the counter tensioner including a fulcrum disposed at the distal end thereof that articulates from an undeployed position to a deployed position to change the angle of the cord as it extends towards the tensioner from the distal end of the counter tensioner.

In example 14, the subject matter of any one of examples 1 to 13 includes the tensioner being operable to tension the cord via a single hand of a user.

In example 15, the subject matter of any one of examples 1 to 14 includes the indicator region of the piston having a greater cross-sectional diameter than any other portion of the piston.

Example 16 is a device for manipulating implants coupled by a cord and/or tensioning a cord extending between at least two implants. The device includes a tensioning having a nose assembly and a cord lock assembly for applying tension to the cord, the nose assembly comprising a piston having a lumen extending therethrough for receiving the cord and a spring positionable in contact with an indicator region of the piston. In this example, the tensioner can be releasably coupleable to a port of a counter tensioner disposed at a distal end thereof and can be releasably coupleable to a head of an implant at a proximal end thereof. In this example, the indicator region is visible through a window in a tensioner main body and indicates cord tension when the nose assembly of the tensioner is coupled to the port of the counter tensioner and engaged with the cord.

In example 17, the subject matter of example 16 includes the nose assembly including a detent releasably coupleable in the port via a capture ball.

In example 18, the subject matter of any one of examples 16 or 17 includes the cord lock assembly having a cord lock housing for engaging the cord disposed at a distal end of an elongate shaft.

In example 19, the subject matter of example 18 includes the cord lock housing including a cam cleat for engaging the cord.

In example 20, the subject matter of any one of examples 18 or 19 includes the elongate shaft being operably coupled to a shaft clutch to drive the elongate shaft distally and a shaft lock to resist return of the elongate shaft in the proximal direction.

In example 21, the subject matter of example 20 optionally includes the shaft clutch is shifted off angle to engage and distally translate the elongate shaft by actuation of a front handle.

In example 22, the subject matter of example 21 includes the front handle being rotatable about pivot axis that is transverse to a longitudinal axis extending from a proximal end to a distal end of the tensioner main body.

In example 23, the subject matter of any one of examples 21 or 22 includes the shaft lock being biased via a distally-located spring to allow distal translation but not proximal translation of the elongate shaft.

In example 24, the subject matter of any one of examples 21 to 23 includes the elongate shaft being distally translated from about 30 mm to about 35 mm during each complete stroke of the shaft clutch.

In example 25, the subject matter of any one of examples 16 to 24 includes the tensioner is operable to tension the cord via a single hand of a user.

In example 26, the subject matter of any one of examples 16 to 25 includes the indicator region of the piston having a greater cross-sectional diameter than any other portion of the piston.

Example 27 is a device for manipulating implants coupled by a cord or for assisting in tensioning a cord disposed between two implants. The device includes a counter tensioner to guide the code from an implant to a tensioning device. The counter tensioner being releasably coupleable to a head of the implant at a proximal end thereof. The counter tensioner is operable to guide the cord to a port proximate the distal end thereof. The counter tensioner can enable translation of the implant relative to another implant implanted in an adjacent or nearby vertebrae. In this example, the counter tensioner includes an elongate body including an inner sleeve and an outer sleeve. In this example, the inner sleeve comprises a plurality of outwardly biased arms at a distal end thereof that are engageable with cooperating features disposed on the head of the implant when the outer sleeve is translated distally over the inner sleeve and at least partially over the head of the implant to urge the plurality of outwardly biased arms into secure engagement with cooperating features of the head of the implant. In this example, the port of the counter tensioner is for receiving a nose assembly of a tensioner.

In example 28, the subject matter of example 27 includes the counter tensioner having a lumen disposed within the elongate body extending from a proximal to a distal end thereof, and wherein a set screw engageable with the head of the implant to fix the cord is deliverable through the lumen.

In example 29, the subject matter of example 28 includes the port being disposed at an angle that is not parallel to a longitudinal axis of the lumen.

In example 30, the subject matter of any one of examples 27 to 29 includes the port including a capture ball releasably coupleable to a detent disposed in the nose assembly of the tensioner.

In example 31, the subject matter of any one of examples 27 to 30 includes the counter tensioner comprising a fulcrum disposed at the distal end thereof to that is actuable from an undeployed position to a deployed position to change the angle of the cord as it extends towards the tensioner from the distal end of the counter tensioner.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b) at the time of filing this application, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention includes:

1. A system for manipulating implants coupled by a cord, the system comprising:
    a tensioner comprising a nose assembly and a cord lock assembly for applying tension to the cord, the nose assembly comprising a piston having a lumen extending therethrough for receiving the cord and a spring positionable in contact with an indicator region of the piston; and
    a counter tensioner to guide the cord from the tensioner to an implant, the counter tensioner comprising an elongate body with a proximal end and a distal end, the proximal end including a port to receive the nose assembly, the distal end releasably coupleable to a head of the implant enabling translation of the implant relative to another implant implanted in an adjacent or nearby vertebrae;
    wherein the indicator region is visible through a window in a tensioner main body and indicates cord tension when the nose assembly of the tensioner is coupled to the port of the counter tensioner and engaged with the cord.

2. The system of claim 1, wherein the counter tensioner has a lumen disposed within the elongate body and extending from the proximal end to the distal end thereof, and wherein a set screw engageable with the head of the implant to fix the cord is deliverable through the lumen.

3. The system of claim 2, wherein the port is disposed at an angle that is not parallel to a longitudinal axis of the lumen.

4. The system of claim 1, wherein the counter tensioner comprises an inner sleeve and an outer sleeve, the inner sleeve comprising a plurality of outwardly biased arms at a distal end thereof that are engageable with cooperating features disposed on the head of the implant when the outer sleeve is translated distally over the inner sleeve and at least partially over the head of the implant to urge the plurality of outwardly biased arms into secure engagement with the cooperating features of the head of the implant.

5. The system of claim 1, wherein the cord lock assembly comprises a cam cleat for engaging the cord disposed at a distal end of an elongate shaft extending longitudinally through the tensioner.

6. The system of claim 5, wherein the elongate shaft is operably coupled to a shaft clutch to drive the elongate shaft distally and a shaft lock to resist return of the elongate shaft in the proximal direction.

7. The system of claim 6, wherein the shaft clutch is shifted off angle to engage and distally translate the elongate shaft by actuation of a front handle.

8. The system of claim 1, wherein the counter tensioner comprises a fulcrum disposed at the distal end thereof that articulates from an undeployed position to a deployed position to change the angle of the cord as it extends towards the tensioner from the distal end of the counter tensioner.

9. A system for manipulating implants coupled by a cord, the system comprising:
a tensioner comprising a nose assembly and a cord lock assembly for applying tension to the cord, the nose assembly comprising a piston having a lumen extending therethrough for receiving the cord and a spring positionable in contact with an indicator region of the piston; and
a counter tensioner to guide the cord from the tensioner to an implant, the counter tensioner comprising an elongate body with a proximal end and a distal end, the proximal end including a port to receive the nose assembly, the distal end of the counter tensioner releasably coupleable to a head of the implant enabling translation of the implant relative to another implant implanted in an adjacent or nearby vertebrae;
wherein the indicator region is visible through a window in a tensioner main body and indicates cord tension when the nose assembly of the tensioner is coupled to the port of the counter tensioner and engaged with the cord.

10. A system of claim 9, wherein the nose assembly includes a detent releasably coupleable in the port via a capture ball.

11. A system of claim 9, wherein the cord lock assembly comprises a cord lock housing for engaging the cord disposed at a distal end of an elongate shaft.

12. A system of claim 11, wherein the cord lock housing comprises a cam cleat for engaging the cord.

13. A system of claim 11, wherein the elongate shaft is operably coupled to a shaft clutch to drive the elongate shaft distally and a shaft lock to resist return of the elongate shaft in the proximal direction.

14. A system of claim 13, wherein the shaft clutch is shifted off angle to engage and distally translate the elongate shaft by actuation of a front handle.

15. A system of claim 14, wherein the front handle is rotatable about a pivot axis that is transverse to a longitudinal axis extending from a proximal end to a distal end of the tensioner main body.

16. A system of claim 13, wherein the shaft lock is biased via a distally-located spring to allow distal translation but not proximal translation of the elongate shaft.

17. A system for manipulating implants coupled by a cord, the system comprising:
a tensioner comprising a nose assembly and a cord lock assembly for applying tension to the cord, the nose assembly comprising a piston having a lumen extending therethrough for receiving the cord and a spring positionable in contact with an indicator region of the piston; and
a counter tensioner to guide the cord from an implant to the tensioner, the counter tensioner being releasably coupleable to a head of the implant at a distal end thereof and operable to guide the cord to a port proximate the proximal end thereof, the counter tensioner enabling translation of the implant relative to another implant implanted in an adjacent or nearby vertebrae, the counter tensioner comprising an elongate body including an inner sleeve and an outer sleeve, the inner sleeve comprising a plurality of outwardly biased arms at a distal end thereof that are engageable with cooperating features disposed on the head of the implant when the outer sleeve is translated distally over the inner sleeve and at least partially over the head of the implant to urge the plurality of outwardly biased arms into secure engagement with cooperating features of the head of the implant.

18. A system of claim 17, wherein the counter tensioner has a lumen disposed within the elongate body extending from the proximal to the distal end thereof, and wherein a set screw engageable with the head of the implant to fix the cord is deliverable through the lumen.

19. A system of claim 18, wherein the port is disposed at an angle that is not parallel to a longitudinal axis of the lumen.

20. A system of claim 17, wherein the counter tensioner comprises a fulcrum disposed at the distal end thereof to that is actuable from an undeployed position to a deployed position to change the angle of the cord as it extends towards the tensioner from the distal end of the counter tensioner.

* * * * *